(12) United States Patent
Mummert et al.

(10) Patent No.: US 7,708,237 B2
(45) Date of Patent: May 4, 2010

(54) FASTENING SYSTEM FOR MEDICAL DEVICES

(75) Inventors: Axel Mummert, Stockelsdorf (DE); Maja Finke, Hamburg (DE); Alexander Mueller, Nuremberg (DE); Sebastian Maier, Erlangen (DE)

(73) Assignee: Dräger Medical AG & Co. KG, Lübeck (DE)

( * ) Notice: Subject to any disclaimer, the term of this patent is extended or adjusted under 35 U.S.C. 154(b) by 582 days.

(21) Appl. No.: 11/680,779

(22) Filed: Mar. 1, 2007

(65) Prior Publication Data

US 2007/0218769 A1    Sep. 20, 2007

(30) Foreign Application Priority Data

Mar. 17, 2006 (DE) .................. 10 2006 012 766

(51) Int. Cl.
  *A47F 5/00*  (2006.01)
  *A47F 7/00*  (2006.01)
  *F16M 11/00*  (2006.01)
  *F16M 13/00*  (2006.01)

(52) U.S. Cl. ............... 248/122.1; 248/121; 248/218.4; 248/220.21; 248/223.41

(58) Field of Classification Search ............... 248/121, 248/122.1, 218.4, 220.21, 223.41, 354.3, 248/125.1, 227.3; 52/36.3; 403/381
See application file for complete search history.

(56) References Cited

U.S. PATENT DOCUMENTS 4,163,537 A * 8/1979 Mourgue ............... 248/188.1
4,356,672 A * 11/1982 Beckman et al. ............ 52/36.6
4,547,092 A * 10/1985 Vetter et al. .................. 403/59
5,074,094 A * 12/1991 Gassler ..................... 52/655.2
5,690,239 A * 11/1997 Ballard ....................... 211/189
6,484,647 B2 * 11/2002 Lininger, Jr. et al. ..... 108/50.01
6,554,235 B1 * 4/2003 Fortier ..................... 248/122.1
6,634,824 B2 * 10/2003 Liu ............................ 403/217
2007/0278360 A1* 12/2007 Chen ......................... 248/121
2008/0251656 A1* 10/2008 Prismall .................... 248/121

FOREIGN PATENT DOCUMENTS

| DE | 198 38 593 A1 | 3/2000 |
| DE | 198 59 473 B4 | 7/2000 |
| DE | 101 96 955 T5 | 4/2004 |
| DE | 103 15 613 B3 | 10/2004 |

* cited by examiner

Primary Examiner—Amy J Sterling
(74) Attorney, Agent, or Firm—McGlew and Tuttle, P.C.

(57) ABSTRACT

A fastening system for medical devices includes a column-shaped interface profile (1) having a lens-shaped cross section with at least one convexly shaped, longer front surface (2) and with two shorter lateral surfaces (3), which are parallel to one another and pass over into the longer front surface (2) via a tappet-shaped projection (4) each. A clamping device (6), fits the longer front surface (2) of the interface profile (1) with the two tappet-shaped projections (4) in a positive-locking manner for fastening medical devices. The clamping device (6) has a concavely shaped outer surface and is provided with clamping jaws (8) that can be set on one side or on both sides for detachable fixation on the interface profile (1). This construction offers the possibility of receiving medical devices and accessories on up to a maximum of four sides simultaneously, especially also via standardized rail elements (7).

20 Claims, 6 Drawing Sheets

FASTENING SYSTEM FOR MEDICAL DEVICES

CROSS REFERENCE TO RELATED APPLICATIONS

This application claims the benefit of priority under 35 U.S.C. §119 of German Patent Application DE 10 2006 012 766.8 filed Mar. 17, 2006, the entire contents of which are incorporated herein by reference.

FIELD OF THE INVENTION

The present invention pertains to a fastening system for medical devices.

BACKGROUND OF THE INVENTION

Various fastening systems for medical devices have become known. For example, a device stand with at least one column for carrying a great variety of means, in which the column can be connected to extension arms with rollers by means of an attachment fitting, appears from DE 198 59 473 B4.

A fastening system for mechanical or electric control components of a medical means at a third object became known from DE 198 38 593 A1, wherein a self-lockingly operating clamping mechanism is provided, which cooperates with a rod-shaped counterpart such that the control component can be fixed at the counterpart in such a way that it is secured against displacement.

SUMMARY OF THE INVENTION

The object of the present invention is to provide a fastening system that can be used in a versatile manner for medical devices, which offers the possibility of fastening only fastening and clamping elements that accurately fit geometrically a uniform interface profile in a positive-locking and non-positive manner, especially without tools.

According to the invention, a fastening system for medical devices is provided. The fastening system comprises a column-shaped interface profile having a lens-shaped cross section with at least one convexly shaped, longer front surface and with two shorter lateral surfaces and with two tappet-shaped projections, the two shorter lateral surfaces being parallel to one another and each transitioning into the longer front surface via a respective one of the tappet-shaped projections. A clamping device is provided fitting the longer front surface of the interface profile with each of the tappet-shaped projections in a positive-locking manner for fastening medical devices, the clamping device having a concavely shaped outer surface and being provided with clamping jaws that can be set on one side or on both sides for detachable fixation at the interface profile.

With the present fastening system with the special column-like interface profile as a carrier element for complementarily fitting clamping devices, there advantageously are a great variety of possibilities of detachably and securely fastening different medical devices and accessories.

As a result, a fastening system is provided, which can be used in a versatile manner and which offers the possibility of receiving medical devices or accessories simultaneously on up to four sides, maximum, especially also via standard rail elements. The clamping device of the fastening system can be mounted horizontally in a simple manner and rapidly and moved vertically in the longitudinal direction of the interface profile. Bringing the clamping device directly into the desired position is possible without mounting into the interface profile. The integrated load-bearing tube element within the interface profile of the fastening system offers the possibility of performing mounting of the fastening system with mobile chassis or stationarily on walls or on the floor as needed.

The fastening system may provide the interface profile with two additional tappet-shaped projections and a cross section of the interface profile that has a biconvex shape with the tappet-shaped projections in the transition area from each of the longer front surfaces to the adjoining, shorter lateral surface, and both the front surfaces and both the lateral surfaces extend mirror-symmetrically in relation to one another.

It is particularly advantageous if the ratio of the distance between the outer surfaces of the lateral surfaces to the maximum distance of the outer surfaces of the front surfaces is approximately 2:1 to 4:1.

The clamping device may comprise a rail element located at a spaced location, for receiving medical devices or accessories. The rail element is preferably of a standardized shape. One or both of the lateral surfaces may advantageously include one or more clamp-on holders. The lateral surfaces may be provided with plug-in or clamp-on cable guide elements. The column-shaped interface profile may include an integrated load-bearing column arranged centrally and used to fix the fastening system.

The column-shaped interface profile may be mounted on a chassis. The chassis may have extension arms with wheels. The extension arms may fold in a horizontal direction. The interface profile is provided with integrated screw-type channels, so that at least one of the additional medical devices, accessories, and a respirator on a support plate can be accommodated at the upper end of the interface profile. The interface profile may be provided with integrated screw-type channels for receiving a supported device at an upper end of the interface profile. The chassis may be used to transport medical devices and accessories.

It may be particularly advantageous for the fastening system to receive lines. The lines may include one of gas-lines, power-lines and data-carrying lines, arranged in the interface profile.

The clamping devices may advantageously have clamping jaws that can be set centrally on both sides. It may be particularly advantageous for the projections of each the lateral surfaces to include bevels of about 45°. The bevels may be located opposite each other.

Exemplary embodiments of the fastening system according to the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
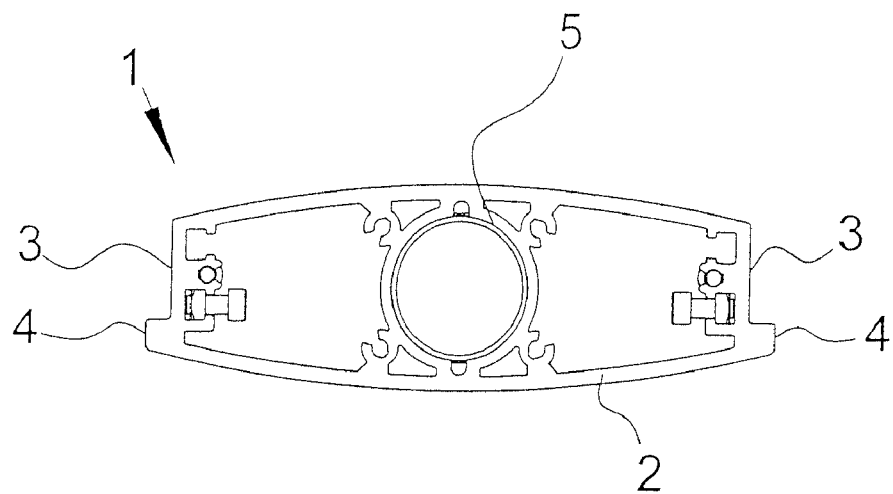
FIG. 1A is a cross sectional view of a column-shaped interface profile of a first embodiment according to the invention.

Referring to the drawings in particular, FIG. 1A shows, in a cross sectional view, the lens-shaped (convex arcuate) interface profile 1. The interface profile 1 is made, for example, of aluminum according to the extrusion method. In the simplest variant of the column-shaped interface profile 1, at least one convexly shaped, longer front surface 2 is provided with two shorter flat lateral surfaces 3, which are parallel to one another and pass over (transition) into the longer front surface 2 via a tappet-like projection 4 each.

Figure 5:
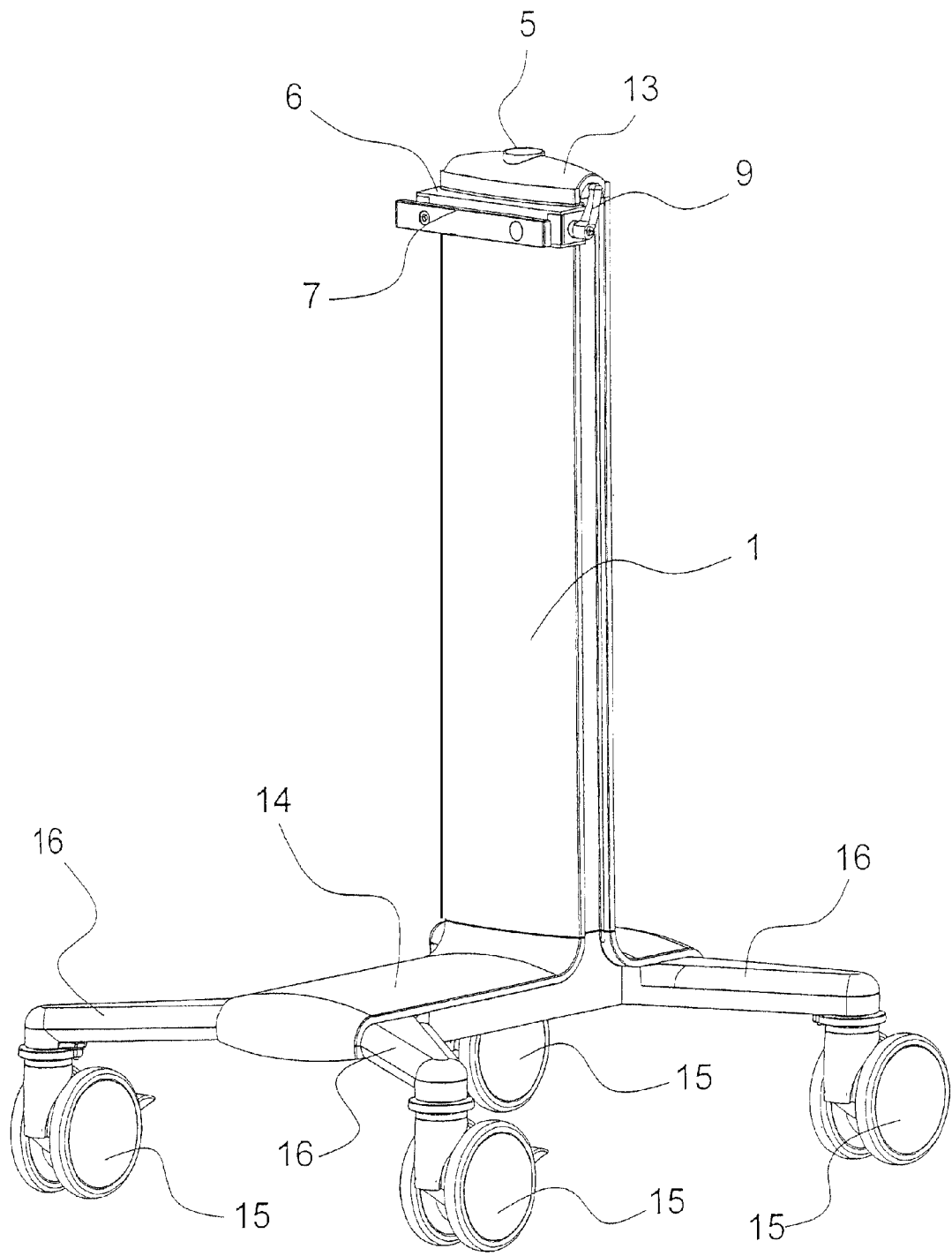
FIG. 5 is a perspective view of a fastening system according to the invention with a chassis used as a transfer cart for medical devices and accessories.

The load-bearing column 5 designed as a tube is accommodated in the interface profile 1 and offers especially the possibility of vertical arrangement in case of mounting, for example, on a mobile chassis (FIG. 5).

Figure 1B:
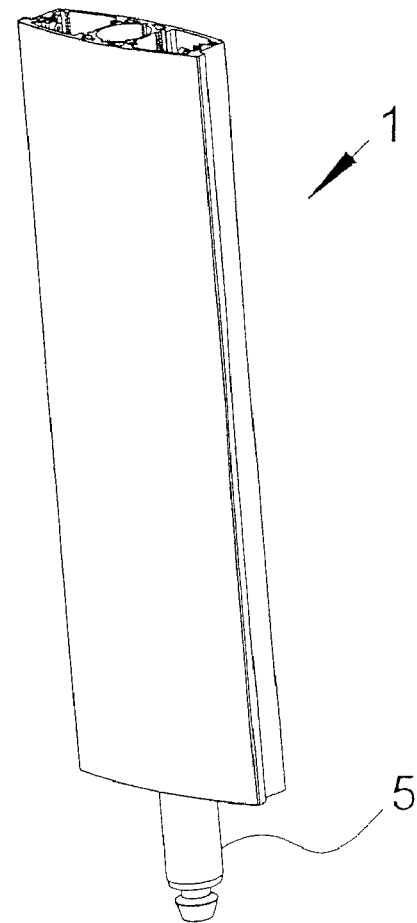
FIG. 1B is a perspective view of the column-shaped interface profile of FIG. 1A.

FIG. 1B shows a view of the column-shaped interface profile 1 which is set up or fastened, in general, vertically, with integrated load-bearing column 5.

Various lines, for example, gas-carrying or energy (power)- or data-carrying lines, may be arranged inside the interface profile 1. The interface profile 1 preferably has integrated screw-type channels, so that additional auxiliary parts can be fastened at the top end; see also FIGS. 6A and 6B.

Figure 2A:
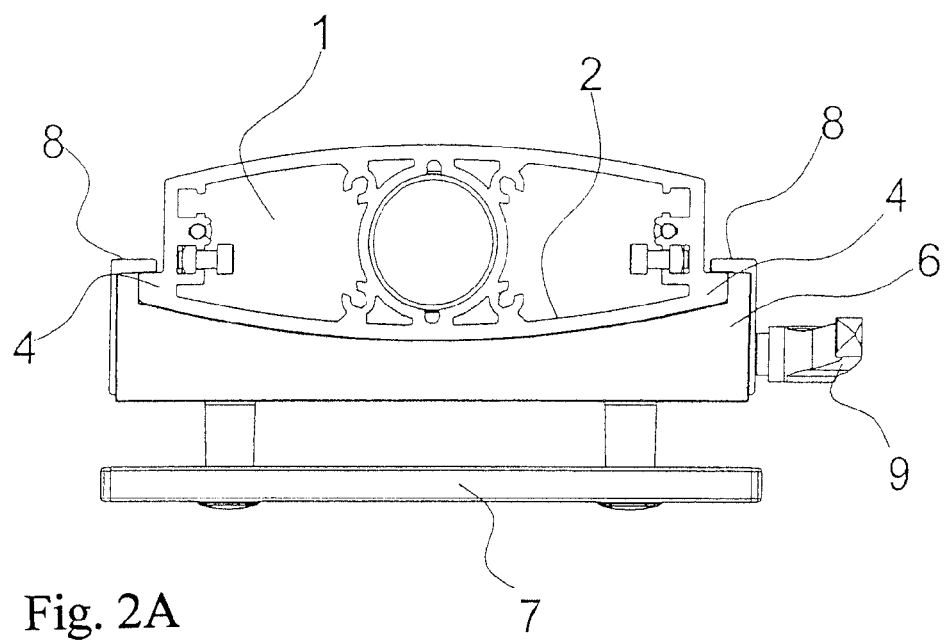
FIG. 2A is a cross sectional view of the interface profile from FIGS. 1A and 1B combined with a clamping device with a rail element.
Figure 2B:
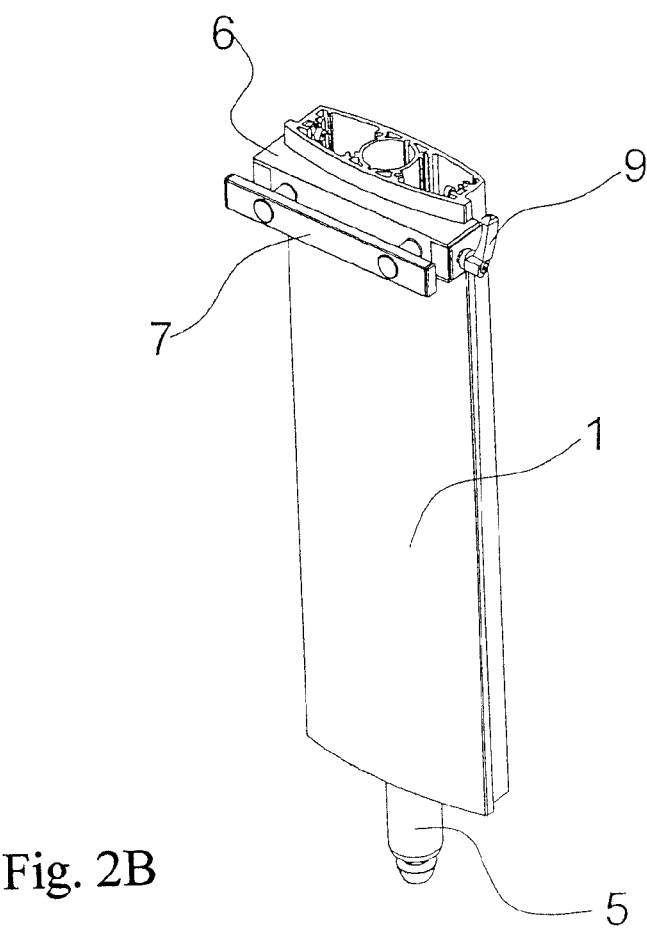
FIG. 2B is a perspective view showing the interface profile from FIGS. 1A and 1B combined with a clamping device at the upper part and showing a load-bearing column in the lower part.

FIG. 2A shows the cross section of an embodiment of the fastening system with the same shown in a perspective view in FIG. 2B. A complementary clamping device 6 with integrated adjusting aid is fastened for better horizontal mounting to the convexly shaped, longer front surface 2 with the two tappet-shaped projections 4 in a positive-locking manner with spring-loaded clamping jaws 8, which are adjustable here on one side by means of a lever 9 without a tool. As an alternative, the clamping device 6 is centrally adjustable on both sides in relation to the clamping jaws 8.

The clamping device 6 can be securely adjusted vertically and can be mounted on the interface profile 1 later at any time, without a medical accessory already present having to be removed before. The clamping device 6 in FIGS. 2A and 2B is equipped with a specially standardized rail element 7, which is suitable for receiving different medical devices or accessories, for example, containers for receiving bronchial secretion, water traps, measuring instruments, and oxygen dispensing means.

Figure 3A:
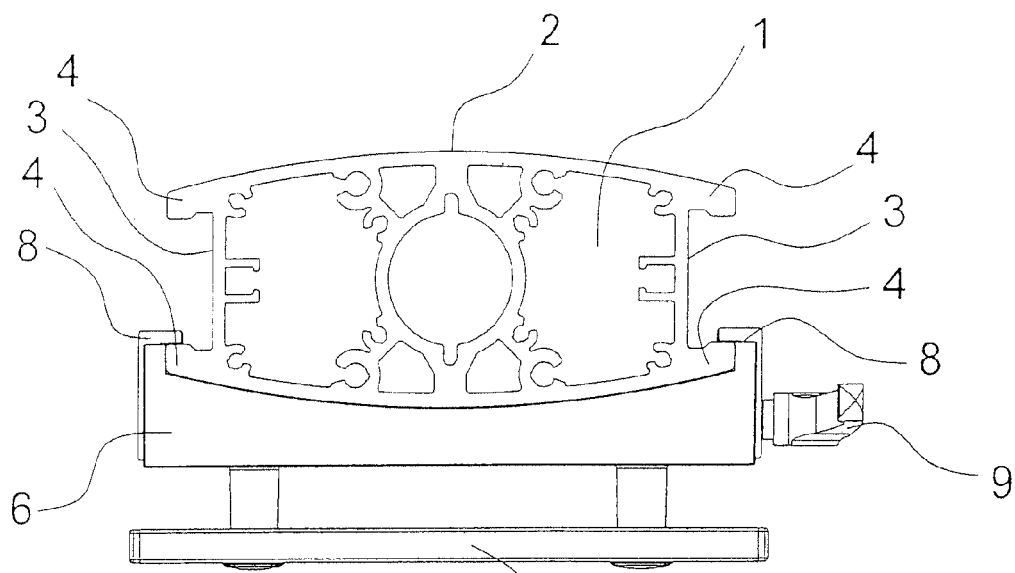
FIG. 3A is a cross sectional view of an interface profile with biconvex contour of a second embodiment according to the invention and showing a clamping device fastened to one of the front surfaces with a rail element in the upper part.
Figure 3B:
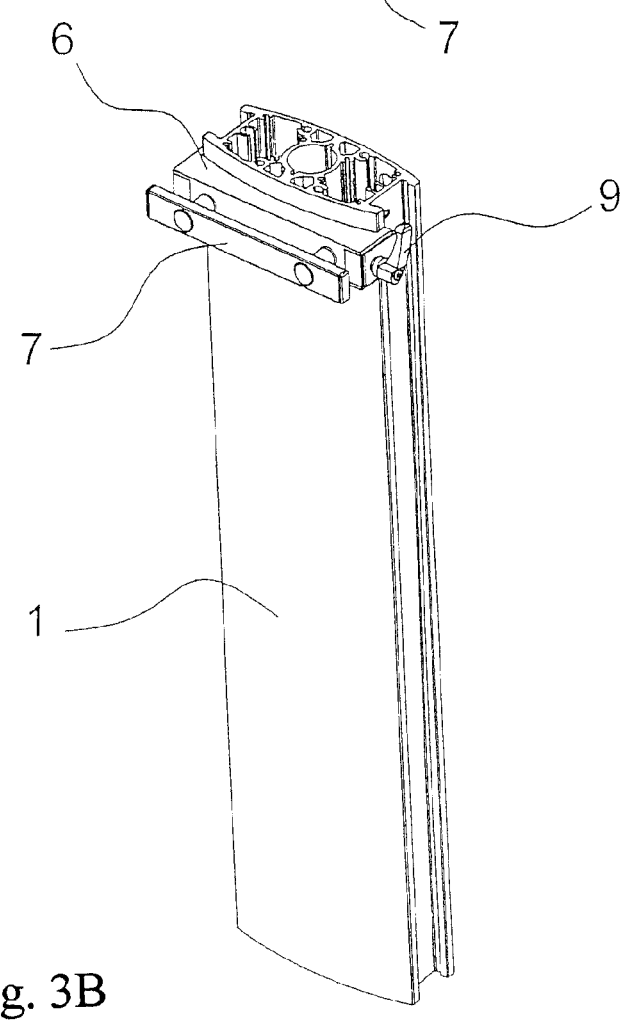
FIG. 3B is a perspective view showing features of the embodiment according to FIG. 3A.

FIG. 3A shows a cross section of a column-shaped interface profile 1 of a biconvex shape with a total of four tappet-shaped projections 4, so that the two longer front surfaces 2 for receiving complementary clamping devices 6 are set up on the two front surfaces 2. In this embodiment, the tappet-shaped projections 4 have, just as in the embodiment shown in FIG. 4, bevels of about 45°, which are located opposite each other, for supporting clamping or gripping elements 12 of holders 10, which are arranged on the lateral surfaces 3.

In addition, the two lateral surfaces 3 may be used to receive additional medical devices or accessories or plug-in or clamp-on cable guide elements.

Figure 4A:
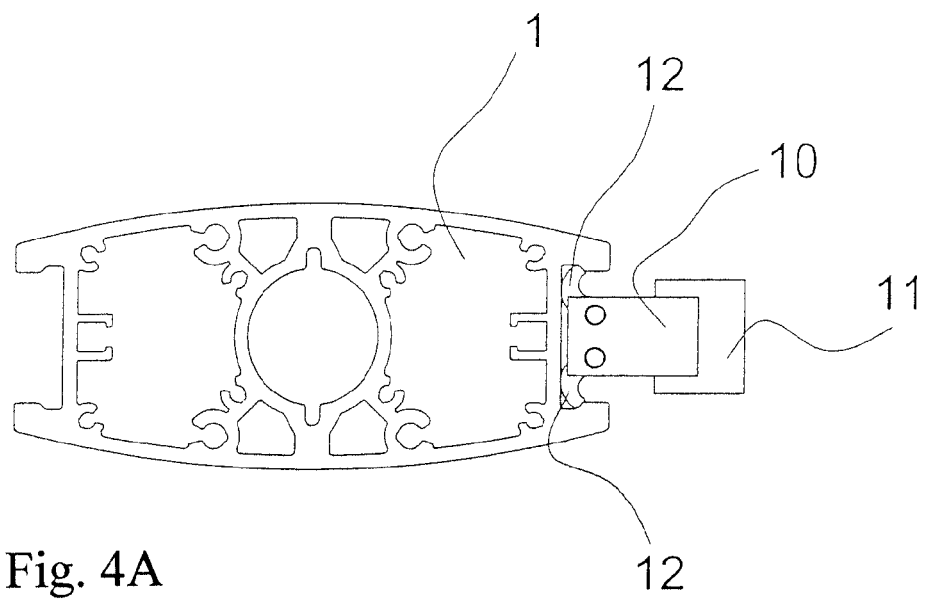
FIG. 4A is a cross sectional view of an interface profile of the embodiment according to FIG. 3A showing a lateral holder on the right-hand, shorter lateral surface thereof.
Figure 4B:
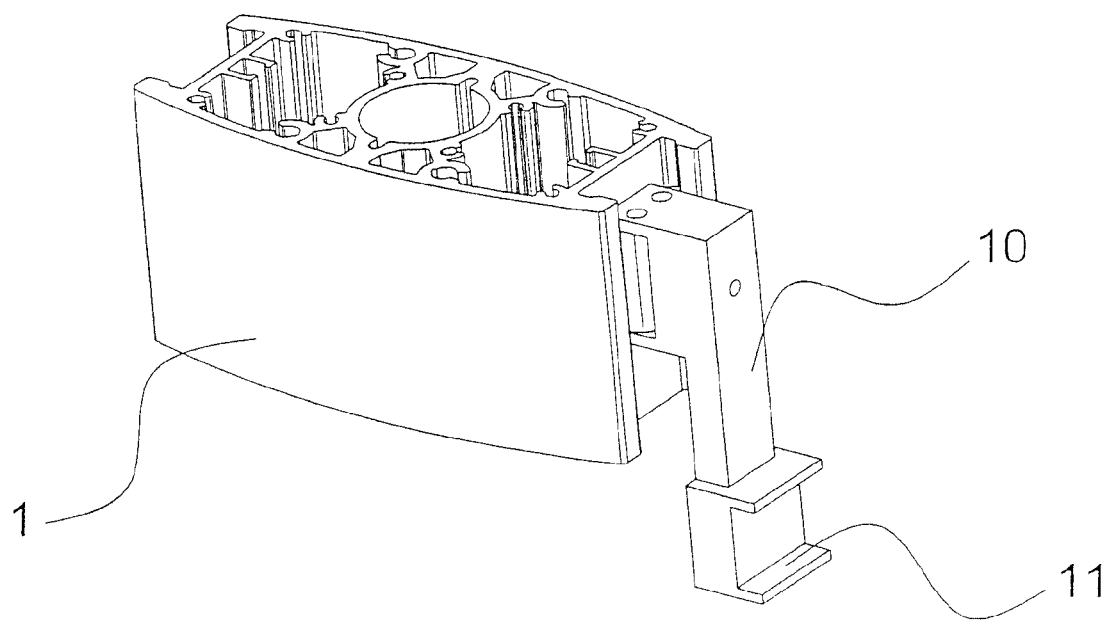
FIG. 4B is a perspective view of the interface profile of the embodiment according to FIG. 3A with the lateral holder.

FIGS. 4A and 4B show the use of a lateral holder 10 with a receiving means 11 for medical accessories. The lateral holder 10 is equipped with spring-loaded, mobile clamping or gripping elements 12, for example, in the form of a dovetail, so that detachable fastening at the shorter lateral surfaces 3 of the interface profile 1 is possible without problems between two tappet-shaped projections 4 with bevels each. As an alternative, the holder 10 is fixed by means of clamping screws against a lateral surface 3 without mounting in the interface profile 1 being necessary. The fastening system has four fastening surfaces suitable for fastening medical devices or accessories, namely, by means of complementary clamping devices 6 for the two longer front surfaces 2 located opposite each other and by means of lateral holders 10 for the two parallel, shorter lateral surfaces 3 located opposite each other.

FIG. 5 shows a view of a fastening system, which is equipped with a chassis body 14 with especially four extension arms 16 for wheels 15. The extension arms 16 may be made with different lengths depending on the use or load situation. The extension arms 16 may also be foldable in the horizontal direction, so that it is possible to adapt the dimensions of the chassis to the special use conditions. The wheels 15 may also be present as double wheels and made rotatable about vertical axes in parallel to the interface profile 1.

A removable cover 13 with a recess for the column 5 for receiving additional accessories, for example, a display screen or a support plate 21 (FIGS. 6A and 6B) for additional medical devices is located in the upper section of the interface profile 1.

Figure 6A:
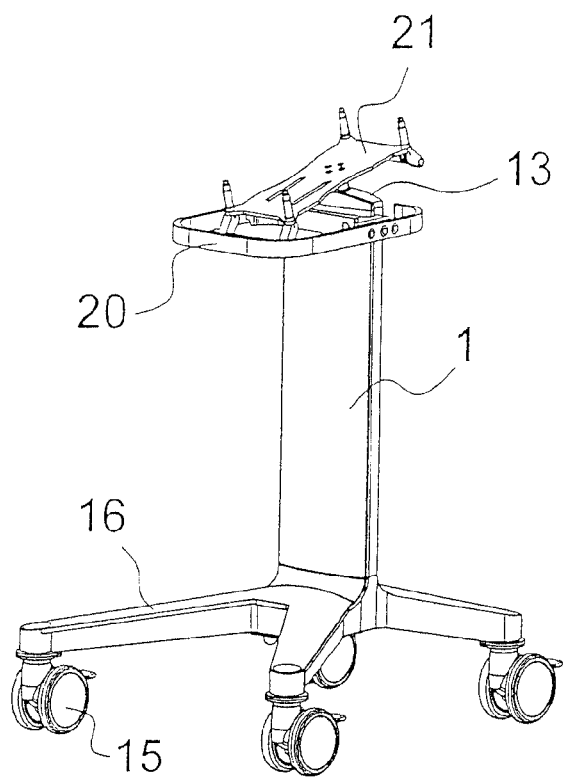
FIG. 6A is a perspective view of the interface profile combined with a chassis.
Figure 6B:
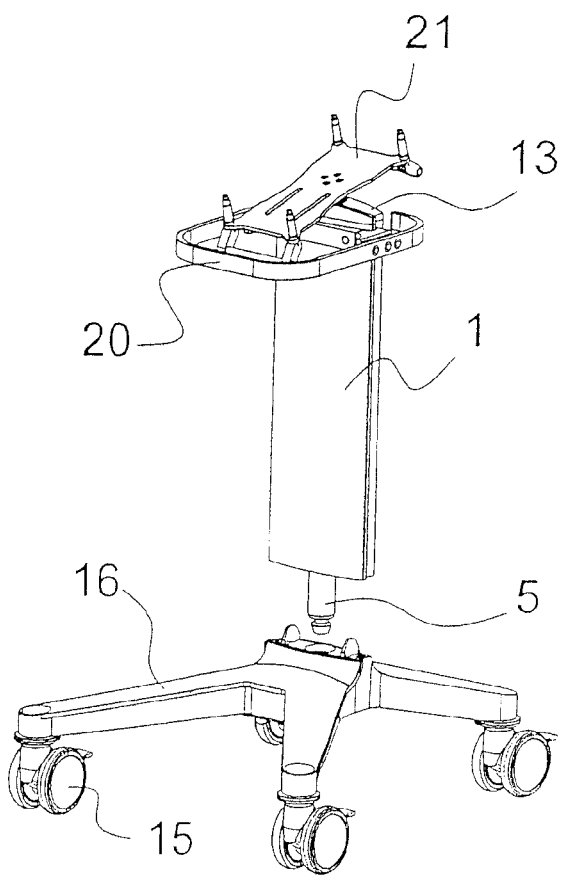
FIG. 6B is a perspective exploded view of the interface profile with chassis.

FIG. 6A shows a view of an assembled interface profile 1 and FIG. 6B shows separately the interface profile 1 combined with a corresponding chassis (in an exploded view).

The interface profile 1 is equipped in the upper section with a holding device 20 and with a support plate 21 for receiving, for example, a helmet respirator, not shown.

The tubular load-bearing column 5 with corresponding connection elements is used to fix the interface profile 1 in the chassis with extension arms 16 and wheels 15 for a mobile transport system for medical devices and accessories.

For example, breathing gas cylinders, breathing gas humidifiers, oxygen generators, exhaust means, water traps, bed adapters, infusion kits and accessories belong to this.

While specific embodiments of the invention have been shown and described in detail to illustrate the application of the principles of the invention, it will be understood that the invention may be embodied otherwise without departing from such principles.

What is claimed is:

1. A fastening system for medical devices, the fastening system comprising:
   a column-shaped interface profile having a lens-shaped cross section with at least one convexly shaped, longer front surface and with two shorter lateral surfaces and with two tappet-shaped projections, said two shorter lateral surfaces being parallel to one another and each passing over into said longer front surface via a respective one of said tappet-shaped projections; and a clamping device fitting said longer front surface of said interface profile with each of said tappet-shaped projections in a positive-locking manner for fastening medical devices, said clamping device having a concavely shaped outer surface and being provided with clamping jaws that can be set on one side or on both sides for detachable fixation at said interface profile.

2. A fastening system in accordance with claim 1, wherein said interface profile has two additional tappet-shaped projections and a cross section of said interface profile has a biconvex shape with said tappet-shaped projections in the transition area from each of said longer front surfaces to said adjoining, shorter lateral surface, and both said front surfaces and both said lateral surfaces extend mirror-symmetrically in relation to one another.

3. A fastening system in accordance with claim 1, wherein the ratio of the distance between the outer surfaces of said lateral surfaces to the maximum distance of the outer surfaces of said front surfaces is approximately 2:1 to 4:1.

4. A fastening system in accordance with claim 1, wherein said clamping device comprises a rail element located at a spaced location, for receiving medical devices or accessories, said rail element being of a standardized shape.

5. A fastening system in accordance with claim 1, wherein one or both of said lateral surfaces include one or more clamp-on holders.

6. A fastening system in accordance with claim 1, wherein said lateral surfaces are provided with plug-in or clamp-on cable guide elements.

7. A fastening system in accordance with claim 1, wherein said column-shaped interface profile includes an integrated load-bearing column arranged centrally and used to fix the fastening system.

8. A fastening system in accordance with claim 7, further comprising a chassis, said column-shaped interface profile being mounted on said chassis, said chassis having extension arms with wheels, said extension arms being foldable in a horizontal direction.

9. A fastening system in accordance with claim 1, wherein said interface profile is provided with integrated screw-type channels, so that at least one of additional medical devices, accessories, and a respirator on a support plate can be accommodated at the upper end of said interface profile.

10. A fastening system in accordance with claim 8, wherein said interface profile is provided with integrated screw-type channels for receiving a supported device at an upper end of said interface profile and wherein said chassis is used to transport medical devices and accessories.

11. A fastening system in accordance with claim 1, wherein lines including one of gas-lines, power-lines and data-carrying lines are arranged in said interface profile.

12. A fastening system in accordance with claim 1, wherein said clamping device has clamping jaws that can be set centrally on both sides.

13. A fastening system in accordance with claim 1, wherein said tappet-shaped projections of each said lateral surface include bevels of about 45°, said bevels being located opposite each other.

14. A fastening system for medical devices, the fastening system comprising:
a column interface profile having a convexly shaped front surface and with two shorter lateral surfaces and with two tappet-shaped projections, said two shorter lateral surfaces being parallel to one another and each transitioning into said longer front surface via a respective one of said tappet-shaped projections; and
a medical device support clamping device with a concavely shaped surface in contact with said convexly shaped front surface and clamping jaws that for detachable fixation at said interface profile for clamping on said tappet-shaped projections to fasten medical devices to said column interface profile.

15. A fastening system in accordance with claim 14, wherein said interface profile has two additional tappet-shaped projections and a cross section of said interface profile has a biconvex shape with said additional tappet-shaped projections in the transition area from said another front surface to said adjoining, shorter lateral surface, and said front surfaces and said lateral surfaces extending mirror-symmetrically in relation to one another.

16. A fastening system in accordance with claim 14, wherein said clamping device comprises a rail element located at a spaced location from said concavely shaped surface, for receiving and supporting medical devices or accessories.

17. A fastening system in accordance with claim 14, wherein said column interface profile includes an integrated load-bearing column arranged centrally and used to fix the interface profile.

18. A fastening system in accordance with claim 14, further comprising a chassis, said interface profile being mounted on said chassis, said chassis having extension arms with wheels, said extension arms being foldable in a horizontal direction.

19. A fastening system in accordance with claim 14, wherein said column interface profile is provided with integrated screw-type channels, so that at least one of additional medical devices, accessories, and a respirator on a support plate can be accommodated at the upper end of said interface profile.

20. A fastening system for medical devices, the fastening system comprising:
a column interface profile having a convexly shaped front surface and with two shorter lateral surfaces and with two tappet-shaped projections, said two shorter lateral surfaces being parallel to one another and each transitioning into said longer front surface via a respective one of said tappet-shaped projections;
a medical device support clamping device with a concavely shaped surface in contact with said convexly shaped front surface and clamping jaws for detachable fixation at said interface profile for clamping on said tappet-shaped projections to fasten medical devices to said column interface profile; and
a chassis, said interface profile being mounted on said chassis, said chassis having extension arms with wheels.

* * * * *